US00PP37268P2

(12) United States Plant Patent
Mccartney

(10) Patent No.: US PP37,268 P2
(45) Date of Patent: Feb. 17, 2026

(54) CHERRY TREE NAMED 'FE'

(50) Latin Name: *Prunus cerasus*
Varietal Denomination: FE

(71) Applicant: Leslie Mccartney, Bozeman, MT (US)

(72) Inventor: Leslie Mccartney, Bozeman, MT (US)

( * ) Notice: Subject to any disclaimer, the term of this patent is extended or adjusted under 35 U.S.C. 154(b) by 0 days.

(21) Appl. No.: 18/831,469

(22) Filed: Jan. 31, 2025

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
CPC ..... A01H 5/085
See application file for complete search history.

*Primary Examiner* — Kent L Bell
(74) *Attorney, Agent, or Firm* — HUESCHEN AND SAGE

(57) ABSTRACT

A tart cherry tree named 'FE' which produces an excellent flavored fruit well suited for fresh eating, as well as for food and juice and wine products. The tart cherry tree named 'FE' may be characterized by its very late fruit harvest and exceptional cold hardiness.

11 Drawing Sheets

Latin name: *Prunus cerasus.*
Variety denomination: 'FE'.
Common name: Tart cherry; Sour cherry; Pie cherry.

BACKGROUND OF THE INVENTION

Tart cherry trees are small trees producing bright red ripe fruit, which fruit is a rich source of polyphenolic compounds, especially proanthocyanins, anthocyanin, and flavanols, all of which are strong antioxidants. Various commercial products derived from tart cherries include nutritional/dietary supplements, food products, and beverage products.

BRIEF SUMMARY OF THE INVENTION

The present invention is a new and distinct variety of tart cherry tree (*Prunus cerasus*) suited to the commercial trade, as well as the homeowner. It is reminiscent of other named tart cherry cultivars known to the inventor producing acceptable quality, flavorful fruits, and having high plant vigor.

Compared with other tart cherry tree cultivars known to the inventor, the tart cherry tree of the present invention produces an excellent flavored fruit. This fruit is well-suited for fresh eating, as well as for food and juice and wine products, and the plant exhibits exceptional cold hardiness.

This invention relates to the discovery and asexual propagation of a new and distinct variety of tart cherry tree, *Prunus cerasus*, named 'FE'.

The tart cherry tree 'FE' bears medium sized bright red fruit on short woody spurs on second year and older wood and is a natural dwarf tree. The fruit and products derived therefrom have a fuller flavor which is sweeter than that of the fruits of tart cherry tree cultivars known to the inventor. The fruits of the tart cherry tree 'FE' may be eaten fresh and without sugar.

Furthermore, the tart cherry tree 'FE' exhibits delayed budding, earlier dormancy and exceptional bud tolerance to cold compared to tart cherry tree cultivars known to the inventor.

The tart cherry tree 'FE' of the present invention originated from new stem growths (i.e. root suckers) from rootstock of the grafted tart cherry tree variety 'North Star' (unpatented), wherein the 'North Star' plant had been propagated by grafting onto rootstock of an unknown cherry tree variety and grown in a cultivated area which has heavy clay soils in Great Falls, Montana, USA. A selected rooted stem (a root sucker) arising from the grafted tart cherry tree variety 'North Star' was prospered into a free, new cherry tree plant, which mature cherry tree plant produced fruits which were different than the fruits of the parent variety 'North Star' and gave rise to a new tart cherry tree variety named 'FE'. These fruits of variety 'FE' in comparison to 'North Star' were slightly smaller, brighter red, and with higher intense flavor and more sweetness.

The tart cherry tree 'FE' was propagated asexually on a farm in Bozeman, MT (1990) by transplanting root suckers from the 'FE' plant grown in Great Falls, Montana, USA. A planting of second, third and fourth generation trees, which were propagated by planting root suckers or root runners from the tart cherry tree 'FE' occurred on the farm in Bozeman, Montana, USA in 2016 and 2017.

The tart cherry tree 'FE' was also propagated asexually in Grand Junction, Michigan USA in 2023 utilizing hardwood cuttings from the first, second and third generations of the 'FE' plant propagated asexually in Bozeman, Montana.

The plant so propagated asexually has shown the unique features of this new *Prunus cerasus* tart cherry tree named 'FE' and are stable and reproduce true to type in successive generations of asexual propagation.

The tart cherry tree 'FE' provides one or more advantages compared to the parental and/or other tart cherry tree varieties known to the inventor. For example, tart cherry tree 'FE' exhibits excellent cold tolerance, is a consistent bearer, has excellent flavor, and has shown resistance to Fire Blight, *Erwinia amylovora*, a bacterial disease which affects fruit trees.

The tart cherry plant tree 'FE' may be characterized by its free flowering without the use of growth regulating chemicals, excellent fruit quality, acceptable resistance to fungal infections, acceptable resistance to insect pests, and ripens over an acceptable period of time to allow for one time fruit harvesting.

The description of the new and distinct variety of tart cherry tree 'FE' based on its flower, fruit, stems, and foliage is based on observations of specimens grown in Bozeman, Montana USA. Horticultural practices have been organic.

In observing the tart cherry tree varieties 'North Star', 'Montmorency' (unpatented), 'Meteor' (unpatented), 'Mesabi' (unpatented), 'Evans' (unpatented) and 'FE', the characteristics of tart cherry tree 'FE' were shown to be outstanding for both commercial use and home garden in comparison to these other tart cherry tree varieties. The tart cherry tree 'FE' is a 9 foot tall by 8 feet wide tree that produces suckers. It is smaller than 'Montmorency' (unpatented), 'Mesabi' (unpatented), 'Evans' (unpatented) and 'Meteor' (unpatented). 'North Star' (unpatented) cherry trees in Bozeman, MT are observed to be larger than the tart cherry tree 'FE'. The tart cherry tree 'FE' of the invention can be easily maintained to a shorter height by pruning and provides an advantage for netting structures and harvesting. The tart cherry tree 'FE' can be trained to an open vase or central leader structure.

The tart cherry tree 'FE' of the invention yields bright-red, medium sized fruit on small spurs. The tart cherry tree 'FE' fruit quality is firm. The fruits are suitable for fresh and process markets. Fresh fruit of the tart cherry tree 'FE' can be stored for 14 days at temperatures 33 to 40 degrees Fahrenheit without deterioration.

The tart cherry tree 'FE' may be characterized as exhibiting midsummer to late summer fruiting, wherein the fruits begin ripening over a twelve-week period after pollination of flowers.

When grown under the same conditions, the tart cherry tree 'FE' blossoms three to four days later than 'Evans' tart cherry tree variety. Late blossoming provides an advantage to the tart cherry tree 'FE' to avoid late spring frosts of the flowers which endangers fruit production.

The new tart cherry tree 'FE' may be characterized by excellent cold tolerance.

The tart cherry tree 'FE' is more tolerant to inclement weather conditions of freezing temperatures than cherry tree varieties known to the inventor. For example, during a harsh winter in a cultivated area in Bozeman, MT the cherry tree varieties, 'Montmorency', 'Mesabi', and 'North Star' died back severely from the winter's erratic temperatures and the trees of the variety 'Evans' survived but yielded no fruit that year. The tart cherry tree 'FE' produced an average yield of fruit that same year.

The tart cherry tree 'FE' has shown cold tolerance to −45 degrees Fahrenheit with minimal, to no tip or blossom bud dieback. When the temperature dipped to the low 20's degrees Fahrenheit during blossom, the tart cherry tree 'FE' still produced a modest crop of cherries. The tart cherry tree 'FE' has produced fruit every year for 30 years in Bozeman, MT, which is a U.S.D.A. Hardiness Zone 3a.

The tart cherry tree 'FE' may be characterized by very late ripening. The fruits of the tart cherry tree 'FE' begin ripening the second to third week of August, in Bozeman, Montana USA, which is one to two weeks after the Canadian Romance series tart cherry tree varieties 'Carmine Jewell' (unpatented), 'Romeo' (unpatented), 'Crimson Passion' (unpatented), and 'Juliet' (unpatented), begin to ripen.

The harvest of the fruit of the new variety 'FE' starts very late in the summer season which is about one to two weeks after 'Carmine Jewel', one week after 'Romeo' and 'Juliet', and three to seven days after 'Evans' varieties.

The fruit of tart cherry tree 'FE' yields a high-quality processed juice described as burgundy red in color with an intense sweet/tart flavor and overtones of almond and red currant. The acid as in all *Prunus cerasus* is present but not overwhelming giving a balanced semi-sweet nose with a tart dry finish flavor that is acceptable to many without added sugar.

Furthermore, the tart cherry tree 'FE' may be characterized by early dormancy and goes dormant three or more days earlier than 'Evans' (see FIG. 1), and 'Lakota' pie cherry tree (see FIG. 2), and always goes fully dormant shedding all its leaves.

Fire Blight, a bacterial disease caused by *Erwinia amylovora*, and which affects fruit trees, has been a problem in Bozeman, MT and the tart cherry tree 'FE' has not been affected by Fire Blight.

The following ratings are on a scale of 1-5, 5 is best.

a. Manageable tree height—5
b. Ornamental value—4
c. Leaf to fruit ratio—5
d. Time of flower—5
e. Time of harvest—5

The following ratings are on a scale of 1-5, 5 is best.

a. Fruit size—4
b. Fruit flavor—5
c. Fruit Firmness—5
d. Pit size—4
e. Fruit drop—5
f. Foliar diseases—4
g. Fruit rots—5
h. Yield—5
i. Uniform ripeness—4

Resistance to diseases and insects: The following ratings are on a scale of 1-5, 5 is best.

a. Black Knot (*Apiosporina morbosa*)—5
b. Brown Rot (*Monilinia fructicola*)—5
c. Cherry Leaf Spot (*Blumeriella jaapii*)—5
d. *Cytospora* Canker (*Cytospora kunzei*)—4
e. Powdery Mildew (*Podosphaera cerasi*)—5
f. Necrotic Ringspot (*Prunus necrotic* ringspot virus (PNRSV))—5
g. Silver Leaf (*Chondrostereum purpureum*)—5
h. *Verticillium* Wilt (*Verticullium dahlia*)—5
i. Crown Rot (*Armillaria mellea*)—5
j. Fire Blight (*Erwinia amylovora*)—5
k. Cherry Slug (*Caliroa cerasi*)—4
l. Cherry Aphid (*Myzus cerasi*)—3

BRIEF DESCRIPTION OF THE DRAWINGS

The accompanying photographs illustrate the overall appearance of the new and distinct variety of tart cherry tree plant 'FE' grown in Bozeman, Montana USA, which tart cherry tree 'FE' is distinguished over tart cherry tree plants known to the inventor and grown under the same conditions.

Figure 1:
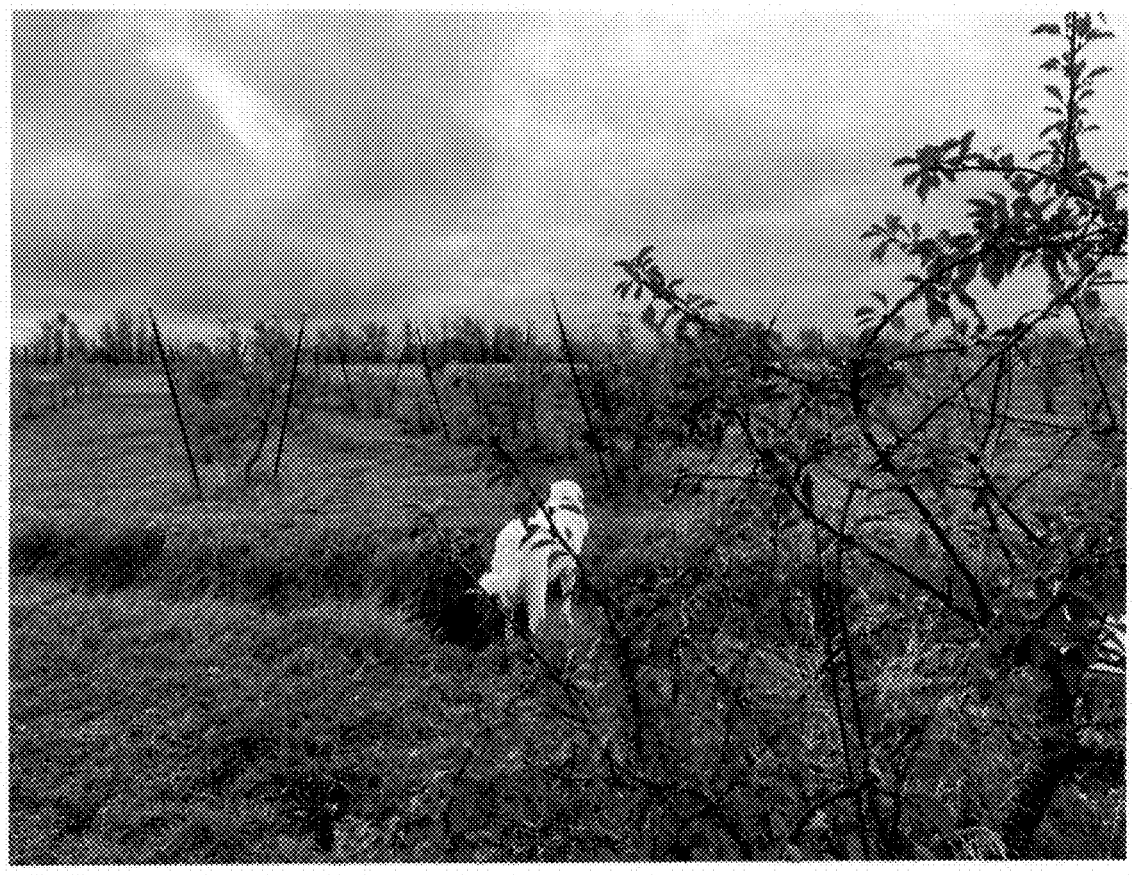
FIG. 1. A photographic illustration of a seven-year-old tart cherry tree 'FE' in the background and an eight-year-old tart cherry tree variety 'Evans' in the foreground on Oct. 12, 2023, showing the tendency of tart cherry tree 'FE' to go dormant earlier than the 'Evans' variety.
Figure 2:
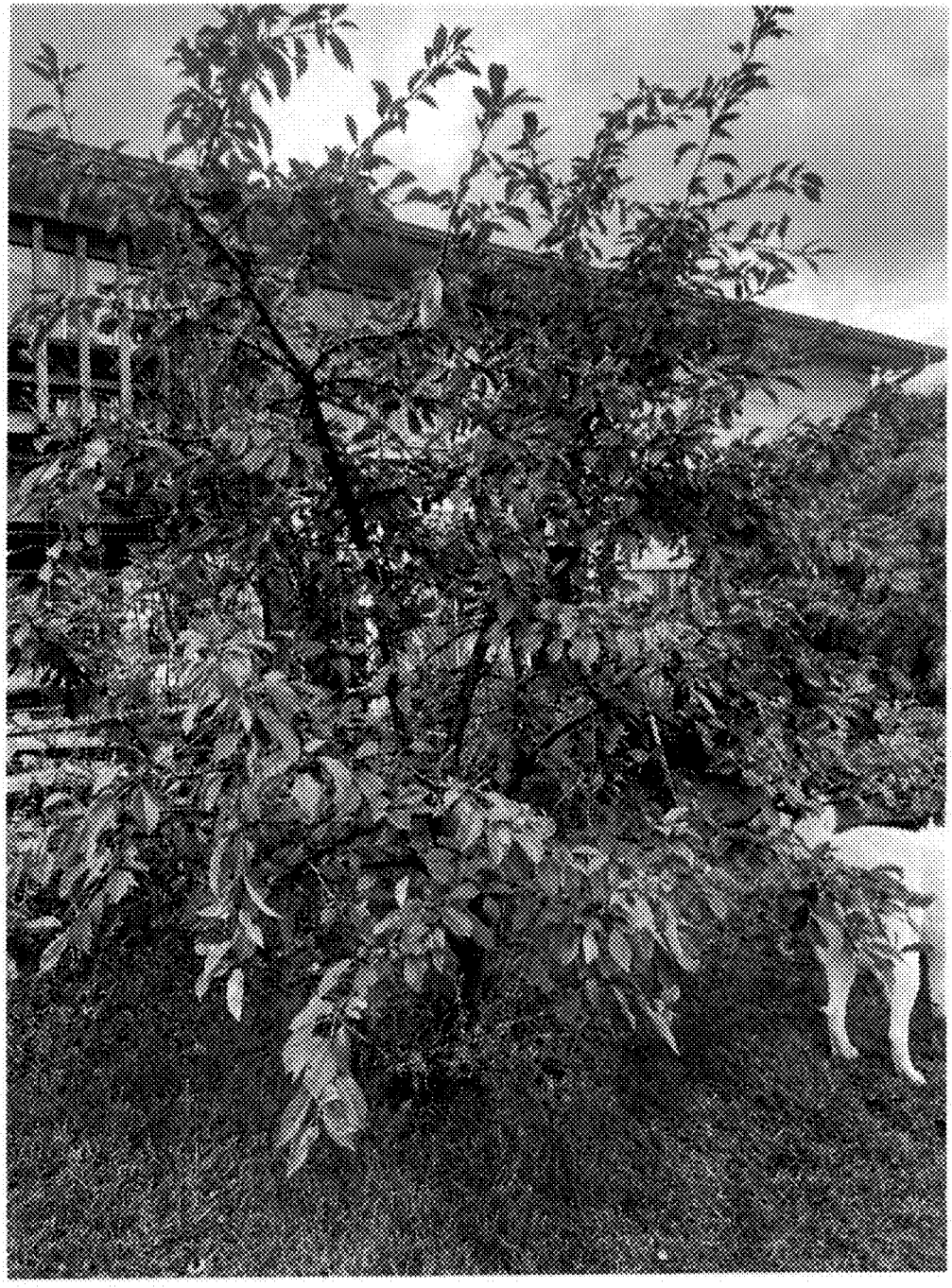
FIG. 2. A photographic illustration of 'Lakota' Pie Cherry on Oct. 12, 2023, wherein the leaves are still fully green.
Figure 3:
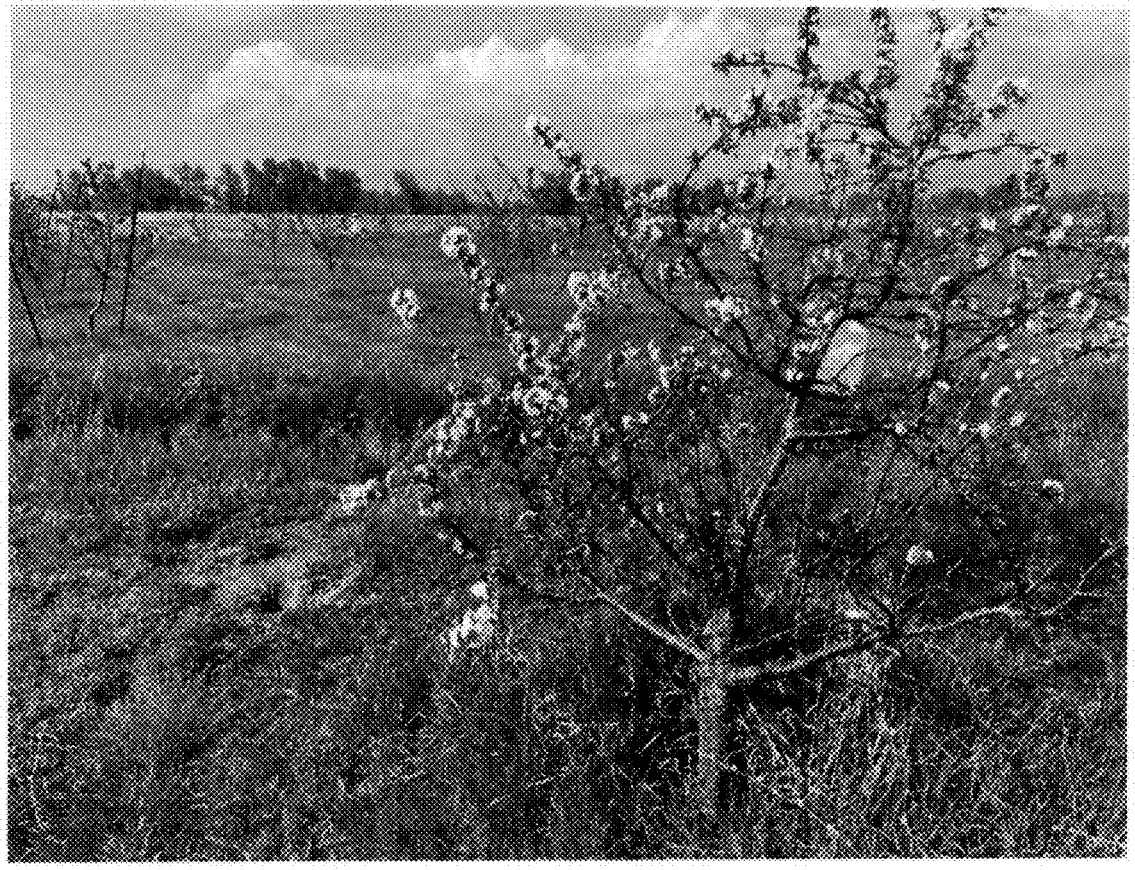
FIG. 3. A photographic illustration of tart cherry tree 'FE' in the background and 'Evans' cherry tree variety in the foreground on May 21, 2023, showing that the tart cherry tree 'FE' is several days behind the 'Evans' cherry tree variety in blooming.
Figure 4:
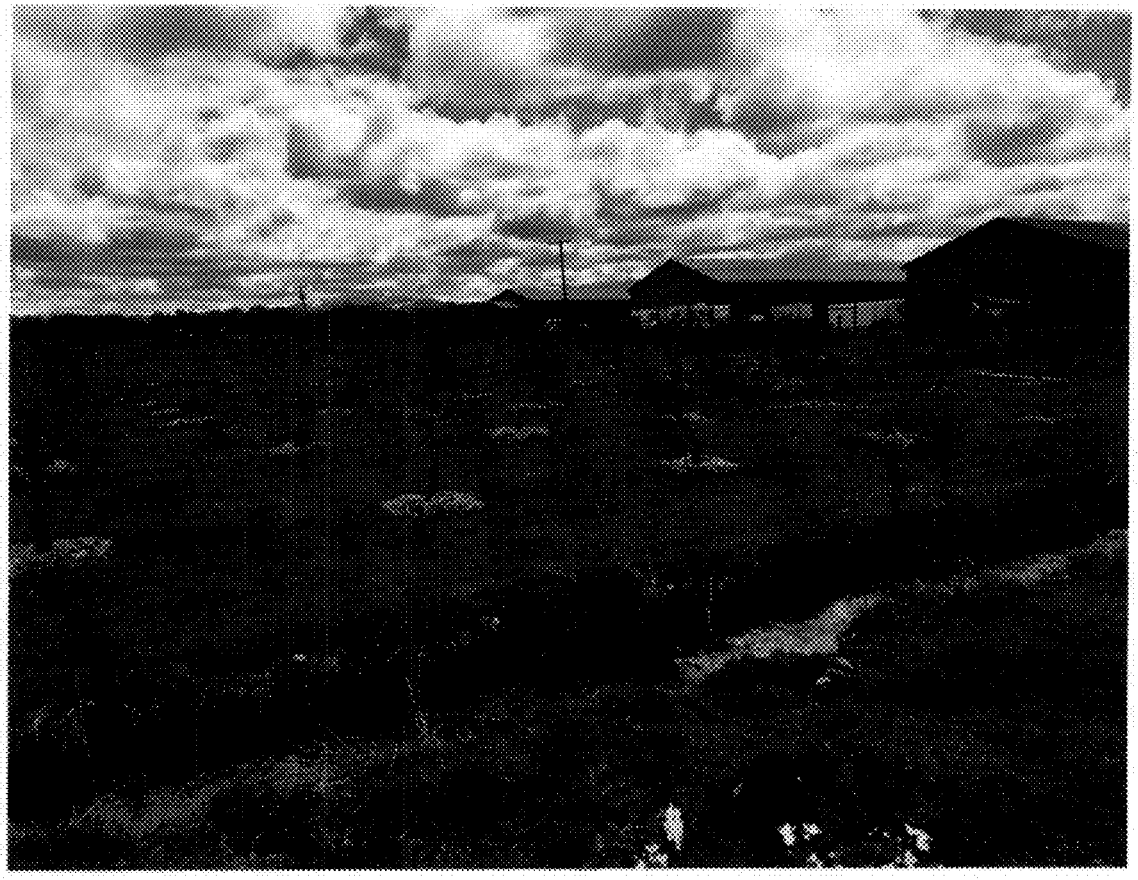
FIG. 4. A photographic illustration showing the tart cherry tree 'FE' starting to bloom on May 24, 2020. Branches of the 'Carmine Jewel' pie cherry tree variety are in the foreground showing the 'Carmine Jewel' variety to be in bloom.
Figure 5:
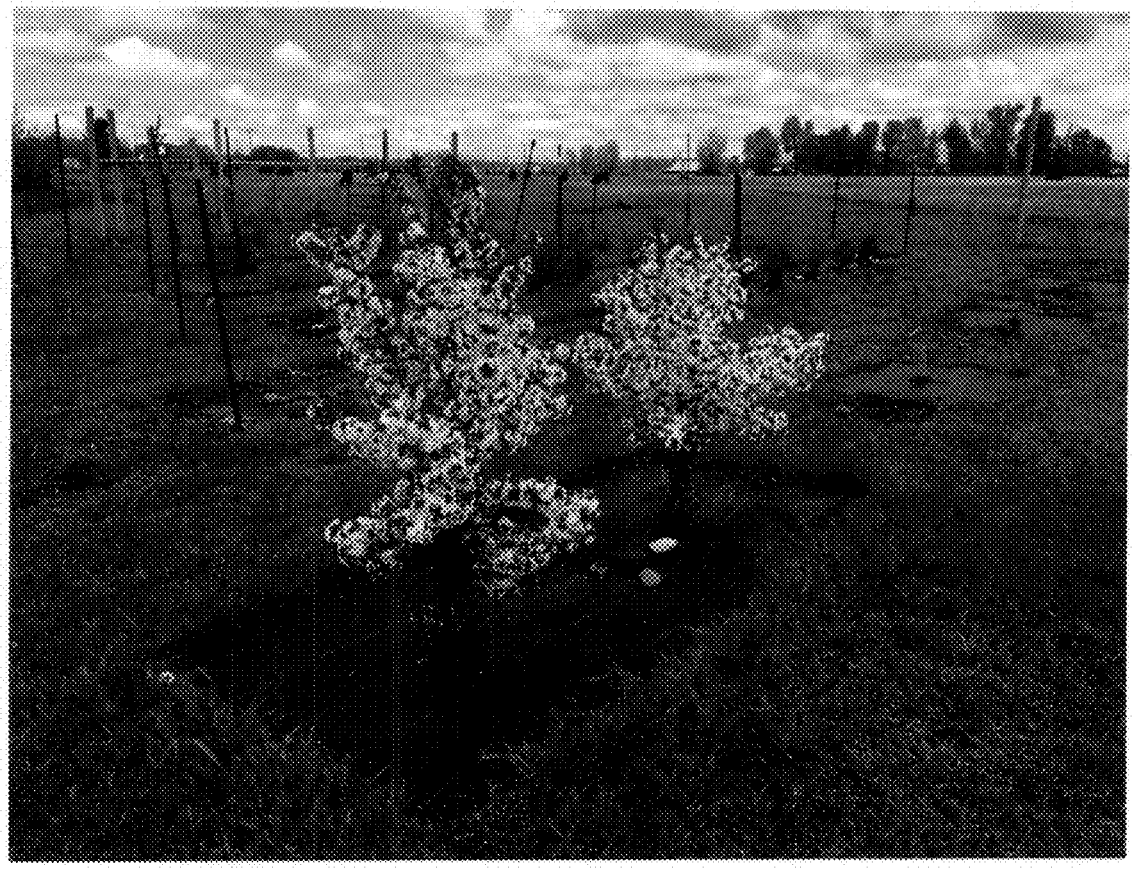
FIG. 5. A photographic illustration showing 'Juliet' cherry tree variety on May 24, 2020 in full bloom several days ahead of the tart cherry tree 'FE'.
Figure 6:
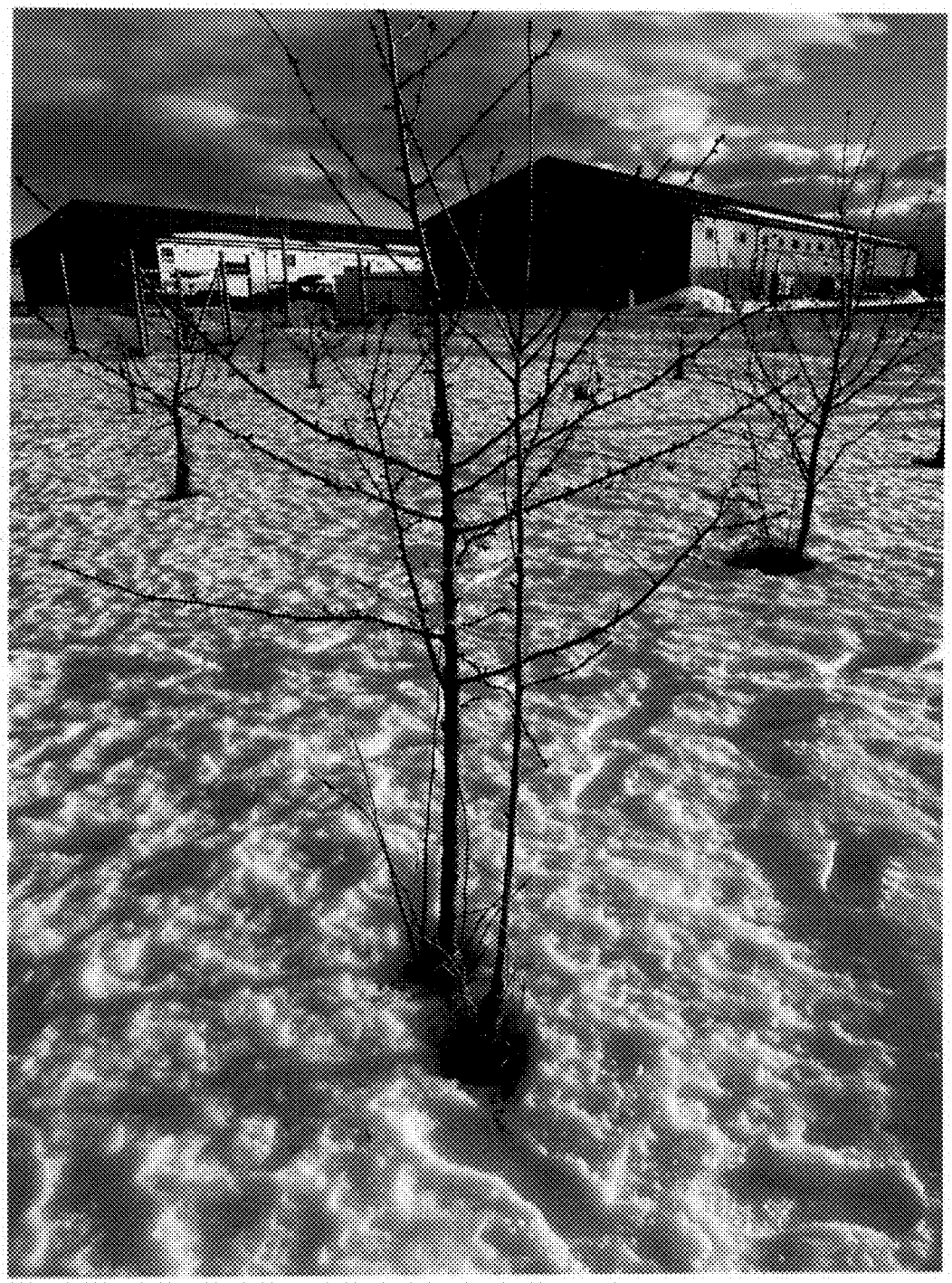
FIG. 6. A photographic illustration of tart cherry tree 'FE' in full dormancy on Dec. 30, 2022.

The following is a detailed botanical description of the new and distinct variety of tart cherry tree 'FE', its flower, fruit, foliage, stems and habit.

DETAILED BOTANICAL DESCRIPTION

Statements of characteristics herein represent exemplary observations of the cultivar herein. Where dimensions, sizes, colors, and other characteristics are given, it is to be understood that such characteristics are approximations and averages. The field observations reported herein are largely based on observations of mature tart cherry tree 'FE' specimens yielding fruits when grown in the vicinity of Bozeman, Montana USA. The specimens were propagated from the original plant and have retained the characteristics of the original selection.

The color determination is in accordance with The R.H.S. Colour Chart published by The Royal Horticultural Society, London, England, 1986, except where general color terms of ordinary dictionary significance are used.

General: The following measurements were from the cherry tree variety 'FE' grown for 10 years in a sandy/gravelly loam soil in Bozeman, Montana, USA. (Data taken during the summer of 2024).

Tree:

*Mature height of plants.*—9 feet (2.74 meter) width 8 feet (2.44 meter).

*Trunk circumference.*—17 inches (43.18 cm) at 5 cm above ground.

*Suckering tendency.*—Yes, with root runners.

*Plant hardiness.*—Cold hardiness in area tested, U.S.D.A. Hardiness Zone 3a. Plant stems and buds are cold tolerant to −45 degrees F. (−42.8 degrees C.) with no bud damage. Winter chilling requirement: standard tart cherry chilling hours of 800 to 1200 hours.

Tree bark color: First year bark is smooth and greyed-orange brown RHS 166 C with light brown specks or lenticels RHS 158D. Second year bark is greyed-orange brown RHS 177 A, rougher texture with horizontal lenticels beginning to form color RHS 158D and blotchy patches of grey color RHS N200D with light brown areas. Three to Six year bark is greyed-orange brown RHS 166 A. Horizontal Lenticels are increasing in size and light brown in color RHS 164A. Ten year and older bark is streaked with patchy areas of RHS 177 A, RHS 177 B and RHS 166 A, with areas of grey surrounding larger horizontal lenticels color RHS 164A. Data for tart cherry tree 'FE' taken in summer of 2024 and fall 2025 in Bozeman, MT, USA. (October data for trunk, branches and shoots was taken in 2025 from an average of trees. Summer data for trunk, branches and shoots was taken in 2024 from an average of trees.)

Trees:

*Type.*—Root runners or suckers taken from 1st and 2nd generation of propagated trees in Bozeman and planted in the orchard in Bozeman, Montana. Pruning on trees used for the following data is Modified Central Leader. The soils sandy loam. These trees have been pruned for height regulation to work with the 8 feet tall netting structures. There are 102 trees in this planting of various ages all true to type.

*Vigor.*—Young trees are vigorous in growth and 5 year and older trees are vigorous in fruit production. New growth slows after 5 years.

*Density.*—Moderate to high if unpruned.

*Form.*—Upright tree with root suckers and fruit emerging around year four.

*Cold hardiness.*—Tested to U.S.D.A. Hardiness Zone 3a,-45degrees Fahrenheit with no bud damage. Temperatures of-50 degrees Fahrenheit produced some tip and bud damage. Tree still produced a crop of fruit.

Trunk:

(*Ten year old tree trunk at* 20 *cm above ground.*).—Diameter — 7.0 cm. Lenticel length — 1.5 cm. Lenticel width — 2.5 mm. Lenticel shape — Elliptic. Lenticel texture — Rough and raised.5 mm. Lenticel color — RHS 164A. Lenticel number — Numerous Lenticels touch each other forming ring-like structures 2 mm high by 60 mm long and spaced around 3 mm apart. Count — 22 in a 5 cm x 5 cm area. Bark color — 90% grey RHS N200D. Secondary bark color — 10% reddish brown patches RHS 177A, RHS 177B and RHS 166A. Bark Texture — Rough.

(*Ten year old tree trunk at* 90 *cm above ground*).—Diameter — 6.5 cm Lenticel length — 1.2 cm. Lenticel width — 2.5 mm. Lenticel shape — Elliptic. Lenticel texture — Rough and raised.5 mm. Lenticel color — RHS 164A. Ring of grey around perimeter of Lenticel RHS N200D. Lenticel number — 13 in a 3.0 cm by 3.0 cm area. Bark color — Reddish brown. RHS 166A with RHS 183A undertone in direct sunlight. Secondary bark color — Grey RHS N200D Grey covers 50% of trunk in blotchy patches. Grey surrounds all branch and spur connections and old node locations. Bark Texture — Rough, grey on edges of curled bark RHS N200D with brown underside RHS 164A.

(*Five year old tree trunk at* 20 *cm above ground.*).—Diameter — 4.0 cm Lenticel length — 75 cm to1.0 cm. Lenticel width — 2.25 mm. Lenticel shape — Elliptic. Lenticel texture — Rough and raised.5 mm. Lenticel color — RHS 164A. Ring of grey around perimeter of Lenticel RHS N200D. Lenticel number — 24 to 30 between nodes, approximately 8.9 cm squared. Bark color — Reddish brown RHS 166A with RHS 166C undertone in direct sunlight. Secondary bark color — Grey RHS N200D. Grey covers 20% in blotchy patches. Bark texture — The red is smooth. The grey is fairly rough and very thin. The grey cracks exposing the reddish brown bark color underneath.

Branches:

(*Data taken first week October* 2025. *Data is averages from multiple trees*.).—Branch angle formed from terminal buds — 70 to 80 degrees. Branch angle formed from apical buds — 30 to 40 degrees. (Branches from apical buds are normally removed during pruning.)

(5 *year old tree branch*).—Diameter at base — 2.6 cm. Length of branch — 120 cm to 140 cm. Lenticel length — 1.1 cm. Lenticel width — 2.5 mm. Lenticel shape — Elliptic. Lenticel texture — Rough and raised.5 mm. Lenticel color — 164 A RHS. Ring of grey around perimeter of Lenticel RHS N200D. Lenticel number — 10 to 12 per 3 cm by 3 cm area. Bark color — Reddish brown RHS183A with RHS 166C undertone in direct sunlight. Secondary bark color — Grey RHS N200D, covers 35% in blotchy patches. Bark Texture — Reddish brown is smooth and shiny, and the grey is dull with a fine roughness. Thin vertical curling beginning with grey RHS N200D on edges.

(3 *year old tree branch*).—Diameter at base — 1.5 cm to 2.0 cm. Length of branch — 80 cm to 90 cm. Lenticel length — 1.5 cm. Lenticel width — 4.0 mm. Lenticel shape — Elliptic. Lenticel texture — Rough and raised.5 mm. Lenticel color — RHS 164A, Ring of grey around perimeter of Lenticel RHS N200D. Lenticel number — Same as new growth average 24 to 30 between nodes, approximately 8.9 centimeters squared. Bark color — Reddish brown RHS 183A with RHS 166C undertone in direct sunlight. Secondary bark color — Grey RHS N200D, thin film surrounding lenticels, old nodes, spurs and base of branches. Bark texture — Smooth except for lenticel bumps.

Shoots: (Data taken first week October 2025. Data is averages from multiple trees.).

(*New shoots on trees before fruit bearing*).—Terminal shoot diameter at base — 4.0 mm to 5.0 mm. Apical shoot diameter at base — 4.5 mm to 5.25 mm. Terminal shoot length — 30 cm to 40 cm. Apical shoot length — 40 cm to 50 cm. Number of nodes on apical shoot — 13 to15.Number of nodes on terminal shoot — 10 to 12. Internode length on apical shoot — 3.0 cm to 4.0 cm. Internode length on terminal shoot — 3.0 cm to 3.5 cm. Lenticel length — 0.5 mm. Lenticel width — 0.5 mm. Lenticel shape — Round Lenticel texture — Rough and raised 0.1 mm. Lenticel color — Yellow RHS 158D Lenticel number — 24 to 30 between nodes, approximately 1.0 cm squared. Bark color — RHS 166C in August, and RHS 174C in October. Secondary bark color — Absent. Bark texture — Smooth.

(*New shoots on trees around* 5 *years of age. Data is averages from multiple trees*.).—Percentage of lateral branches with new tip growth — 70%. Mostly the lower branches are without new shoot growth. Terminal shoot diameter at base — 3.5 mm to 4.5 mm. Apical shoot diameter at base — 4.5 mm to 5.0 mm. Terminal shoot length — 20 cm to 30 cm. Apical shoot length — 30 cm to 35 cm. Number of nodes on apical shoot — 10 to 11. Number of nodes on terminal shoot — 9 to 10. Internode length on apical shoot — 2.5 cm to 4.0 cm. Internode length on terminal shoot — 2.0 cm to 3.5 cm. Lenticel length — 0.5 mm. Lenticel width — 0.5 mm. Lenticel shape — Round. Lenticel texture — Rough and raised 0.1 mm. Lenticel color — RHS 158D. Lenticel number — 24 to 30 between nodes, approximately 0.56 cm squared. Bark color — RHS 166C in August, and RHS 174C in October. Secondary bark color — Absent. Bark texture — Smooth.

(*New shoots on trees around* 10 *years of age*).—Percentage of lateral branches with new tip growth — 50%. Terminal shoot diameter at base — 2.5 mm to 3.0 mm. Apical shoot diameter at base — 2.5 mm to 3.25 mm. Terminal shoot length — 5 cm to 15 cm. Apical shoot length — 10 cm to 20 cm. Number of nodes on apical shoot — 7 to 10. Number of nodes on Terminal shoot — 7 to 10. Internode length on apical shoot — 1.5 cm to 2.5 cm. Internode length on terminal shoot — 1.5 cm to 2.5 cm. Lenticel length — 1.0 mm. Lenticel width — 1.0 mm. Lenticel shape — Round. Lenticel texture — Rough and raised 0.1 mm. Lenticel color — RHS 158D. Lenticel number — 24 to 30 between nodes approximately 0.35 cm squared. Bark color — RHS 166C in August, and RHS 174C in October. Secondary bark color — Absent. Bark texture — Smooth.

(*Before fruit bearing up to three years of age, and new shoot growth on older tree branches. Data taken October* 2025. *Data is averages from multiple trees*.).—Buds and woody spurs — All buds are mixed buds producing leaves, flowers and shoots and are regulated by the tree as to what they produce. Terminal bud count — 1 per node. Apical bud count — 3 per apical node, sometimes 2. Terminal Bud size — Length 4.5 mm, width 2.2 mm. Apical center bud size — Length 4.5 mm, width 2.5 mm. Apical side bud size — Length 3.0 mm, width 2.0 mm. Scales present — Yes three rows. Bud shape — Ovate with apex pointed but not sharp. Bud color — RHS 164A.

(*After fruit bearing begins. Data taken October* 2025. *Data is averages from multiple trees*.).—Bud count average — Five per spur, usually 3 larger and 2 smaller. Varies from 2 to 8 buds per spur. Larger bud size — Length 4.5 mm, width 2.3 mm. Smaller bud size — Length 3.0 mm, width 1.7 mm. Scales present — Yes three rows. Bud color — RHS 164A. Bud size on short shoots that emanate from a spur — Length 4.5 mm, width 2.3 mm. Spur, color of elongated portion — Mostly grey RHS 201B peppered with black RHS 202A and small patches of red RHS 176A. Spur shape — Elongated shape like stacked flattened spheres. Each years growth adds a new flattened sphere. Some spurs will add a short new shoot growth with several nodes, these nodes become spurs creating a branched spur. Spur texture — Spurs are woody and rough. Spur diameter — 4 mm to 5 mm. Spur growth per year — 3 mm to 4 mm.

Mature leaves:

*Length.*—6.0 cm to 8.0 cm.
*Width.*—3.0 cm to 5.0 cm.
*Shape.*—Elliptic.
*Apex.*—Acuminate.
*Base.*—Cuneate and slightly oblique.
*Margin.*—Serrate with rounded tips.
*Surface texture* (*both upper and lower leaves*).—Smooth
*Color upper surface spring.*—RHS 137C.
*Color lower surface spring.*—RHS 144A.
*Color upper surface summer.*—RHS 137A.
*Color lower surface summer.*—RHS 146A.
*Texture both sides.*—Smooth. Venation pattern — Pinnate.
*Vein color lower.*—RHS 144C.
*Vein color upper.*—RHS 144C at the base and blending into the leaf color at the tip, RHS 137A summer color, and RHS 137C in the spring.
*Petiole color.*—RHS 144C.
*Petiole length.*—4.0 cm to 4.5 cm.
*Petiole diameter.*—2.5 mm.
*Petiole texture.*—Smooth.
*Glands.*—Number: 2, occasionally 1 or absent. Shape is round.5 mm diameter with hole in center. Color is RHS175C. Occasionally the center is darker RHS 187A.
*Gland texture.*—Smooth.
*Stipule.*—Normally absent. Occasionally occurs one side. — Color — RHS 144C, with serrate edges.
*Stipule length and width.*—Length 6.5 mm. Width at base — 1.5 mm.
*Stipule texture.*—Smooth.
*Leaves fall color.*—Transitions from RHS 164B or RHS 164C to RHS N170A to RHS 180B.
*Petiole fall color.*—Red RHS 184C.
*Leaves on new shoot growth.*—Length — 7.0 cm to 13 cm. Width — 4.0 cm to 6.5 cm. Petiole length — 3.5 cm average. Petiole diameter — 3.5 mm.

Flower:

*Corolla shape.*—Cup shaped with 5 pedals in a rotate form.
*Diameter of fully open flower corolla.*—20 mm.
*Depth of fully open flower corolla.*—8 mm.
*Relative positions of petal margins.*—Slightly overlapping.
*Quantity per cluster or spur.*—10 to 12 average.
*Pedicel length.*—18 mm.
*Pedicel diameter.*—1 mm.
*Pedicel texture.*—Smooth.
*Pedicel color.*—RHS 144C.
*Date of first bloom* 2023 *growing season.*—May 19 to May 21.
*Date of full bloom* 2023 *growing season.*—May 26 to 29.
*Total days of bloom time* 2023 *growing season.*—12 days. Seasonal changes do not change the length of bloom time, but can change its timing by two weeks earlier to two weeks later. All other fruit follows the same pattern.
*Fragrance.*—High.

Petals:

*Number per flower.*—5.
*Length.*—10.0 mm.
*Width.*—8.5 mm.
*Petal shape.*—Oval and slightly cupped.
*Apex shape.*—Emarginate.
*Base shape.*—Rounded.
*Margin.*—Entire, slightly ruffled.
*Upper surface color.*—White RHS NN155D.
*Lower surface color.*—White RHS NN155D.
*Texture upper surface.*—Smooth.
*Texture Lower surface.*—Smooth.

Pistil:

*Pistil length.*—10.4 mm.
*Pistil diameter at base.*—4.6 mm.
*Pistil color.*—RHS 144C.
*Pistil texture.* Glabrous.
*Pistil end shape.*—Cup shaped from side view with a ruffled top. Top view is emarginate.
*Pistil depth.*—1.0 mm.
*Pistil width of stem cavity.*—1.5 mm.
*Pistil position.*—One quarter of the anthers are above, and three quarters of the anthers are below.
*Stigma diameter.*—1 mm.
*Stigma color at anthesis.*—RHS 151A.
*Style length.*—8.2 mm.
*Style color.*—RHS 150B.
*Ovary length.*—2.2 mm.
*Ovary diameter.*—1.5 mm.
*Ovary color.*—RHS 149A.

Stamens:

*Filament number.*—31 to 35.
*Filament length.*—8.3 mm.
*Filament color.*—White RHS NN155D.
*Anther color.*—RHS 23A.
*Pollen color.*—RHS 23D.
*Pollen amount.*—Moderate.

Sepals:

*Quantity per flower.*—5.
*Length.*—4.5 to 5.0 mm.
*Width.*—3.0 mm at base, 1.6 mm at tip.
*Shape.*—Slightly cupped with a broad base. Apex is rounded and narrower; margin is serrate and ruffled.
*Position.*—Alternate with petals. Adpressed to the receptacle.
*Lower color.*—Green RHS 139C. Red blush commonly found at base — RHS 46A
*Upper color.*—Green RHS 139 C.
*Texture.*—Smooth both sides.

Receptacle:

*Depth.*—6.5 mm.
*Width.*—4.25 mm.
*Color.*—Green RHS 139C. Red blush commonly found on one side RHS 46A.
*Texture.*—Smooth.

Fruit:

*Quantity per cluster or spur.*—Average of 10 to 12.
*Relative size.*—Medium.
*Length.*—19.0 mm average
*Width.*—20.0 mm. average.
*Shape.*—Globose.
*Weight.*—5.3 g average.
*Form viewed from apex.*—Round.
*Stalk cavity depth.*—1.5 mm.
*Stalk cavity diameter.*—6.0 mm.

*Stem Length.*—2.5 cm to 3.5 cm.
*Stem diameter.*—1.5 mm.
*Stem color.*—Green RHS 144D. Red speckled blush RHS 44A at base of stem. RHS 44A blush is sometimes found at top of stem and will sometimes completely covers the stem as the fruit goes from ripe to very ripe.
*Stem texture.*—Smooth.
*Stem adhesion to stone.*—Firmly adhered to stone until fully ripe, then moderate. Fruit easily separates from the stem, but seldom falls to the ground.
*Stem adhesion to spur.*—Always firm.
*Suture.*—Absent.

Fruit flesh:
*Firmness.*—Firm.
*Texture.*—Creamy, fine. Mildly firm.
*Flavor.*—Excellent with pleasant acid/sugar balance.
*Juiciness.*—Very juicy.
*Brix at first ripe stage.*—16%.
*Brix at fully ripe stage.*—19%, often reaches 20% to 23%.
*Aroma.*—Mild
*Flesh color at first ripe.*—RHS 164C.
*Flesh color at fully ripe.*—RHS 46A. Color goes from yellow to red when fully ripe.
*Juice color.*—Processed, RHS 185A, fresh RHS 46A.
*Titratable acidity.*—13.9 g/L Malic Acid eq. pH 3.36.
*Fruit fibers number and length.*—Fibers do not stay attached to the pits even with careful extracting of the pit. Their number and length could not be observed.

Fruit skin:
*Thickness.*—Thin.
*Texture.*—Smooth.
*Color at first ripe.*—RHS 46A.
*Color at fully ripe.*—RHS 60A.
*Tendency to split.*—Seldom.
*Lenticels.*—Lenticels can be observed under magnification but are not seen with the eye.
*Lenticel quantity.*—Numerous.

Stone:
*Length.*—10.6 mm
*Width.*—7.4 mm.
*Thickness.*—5.3 mm.
*Shape.*—Elongated.
*Surface texture.*—Finely porous with ridges where the halves join. Apex is pointed and base is emarginate.
*Color.*—RHS 164C.
*Tendency to split.*—None.

Harvest maturity: Very Late, Mid-to Late-August in Bozeman, MT; September 16 was also a very late picking of very mature fruit. Harvest season 2023 was August $15^{th}$ to August $27^{th}$ (ripe and very ripe season pick dates).

Productivity: Yields up to 30 pounds (13.6 Kg) of berries per plant per year at plant maturity.

Use: Fresh and processed. Excellent for juice, wine, pies, jams and jellies or fresh consumption.

Shipping quality: Moderate.

Storability: Moderate, can be stored for 14 days at temperatures 33 to 40 degrees F. (0.5 to 4.4 degrees C.).

Marketing: The fruit is suitable for fresh marketing.

Susceptibility and resistance: In observing the plants for 30 years in Montana it is concluded that the plants have resistance to the following fungal diseases: Fire Blight (*Erwinia amylovora*), Black Knot (*Apiosporina morbosa*), Brown Rot (*Monilinia fructicola*), Cherry Leaf Spot (*Blumeriella jaapij*), Powdery Mildew (*Podosphaera cerasi*), Necrotic Ringspot (*Prunus necrotic* ringspot virus), Silver Leaf (*Chondrostereum purpureum*), *Verticillium* Wilt (*Verticillium dahlia*), Crown Rot (*Armillaria mellea*).

What is claimed is:

1. A new and distinct variety of cherry tree named 'FE' substantially as herein described and illustrated.

* * * * *

(A)

Figure 7:
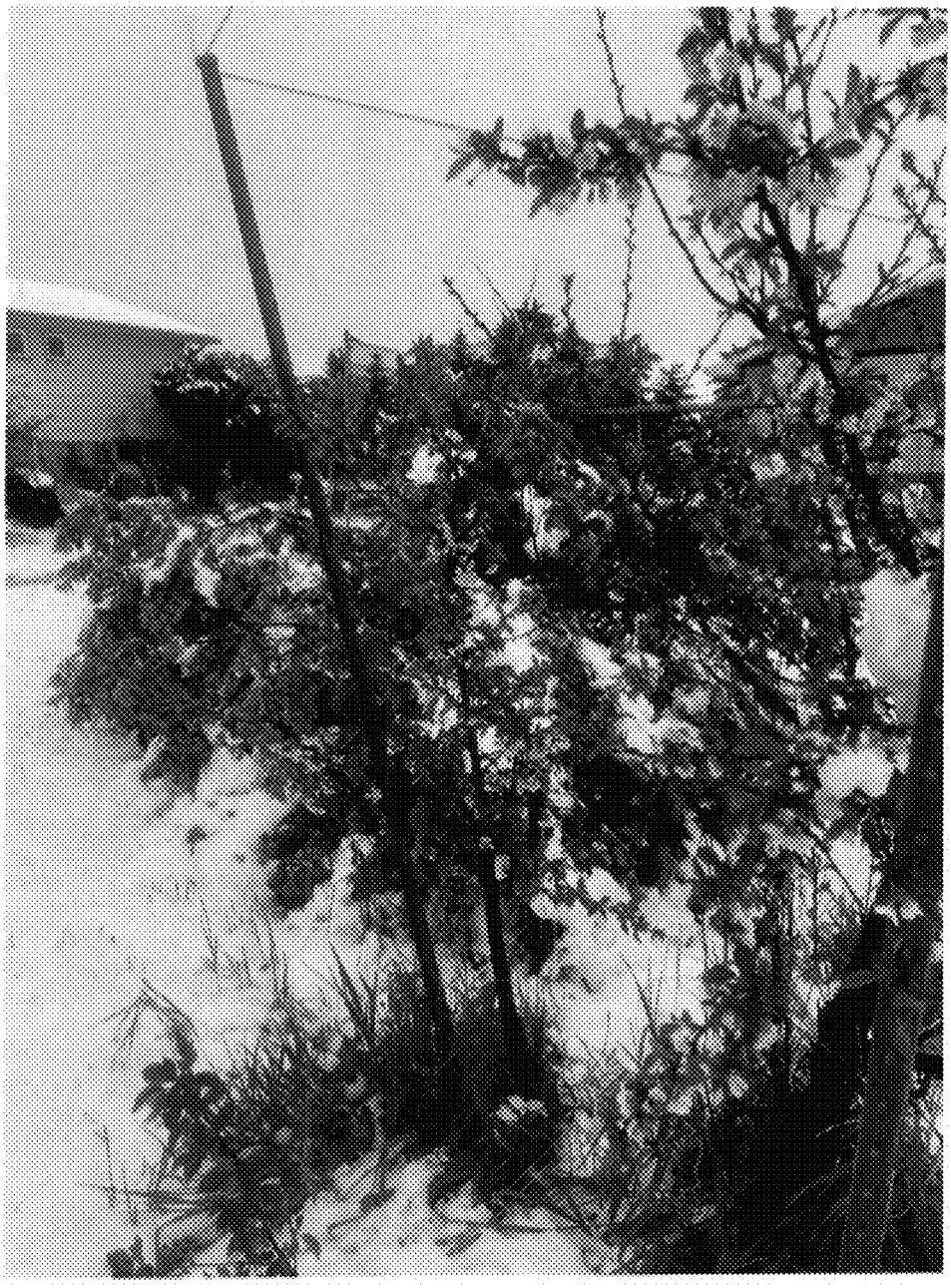
FIG. 7. (A) A photographic illustration showing the tart cherry tree 'FE' partially in bloom on May 23, 2024 when the temperature dipped to the low 20's degrees Fahrenheit. (B) A photographic illustration of the tart cherry tree 'FE' in (A) after May 23, 2024 showing minimal freeze damage to the buds and cold hardiness.
Figure 8:
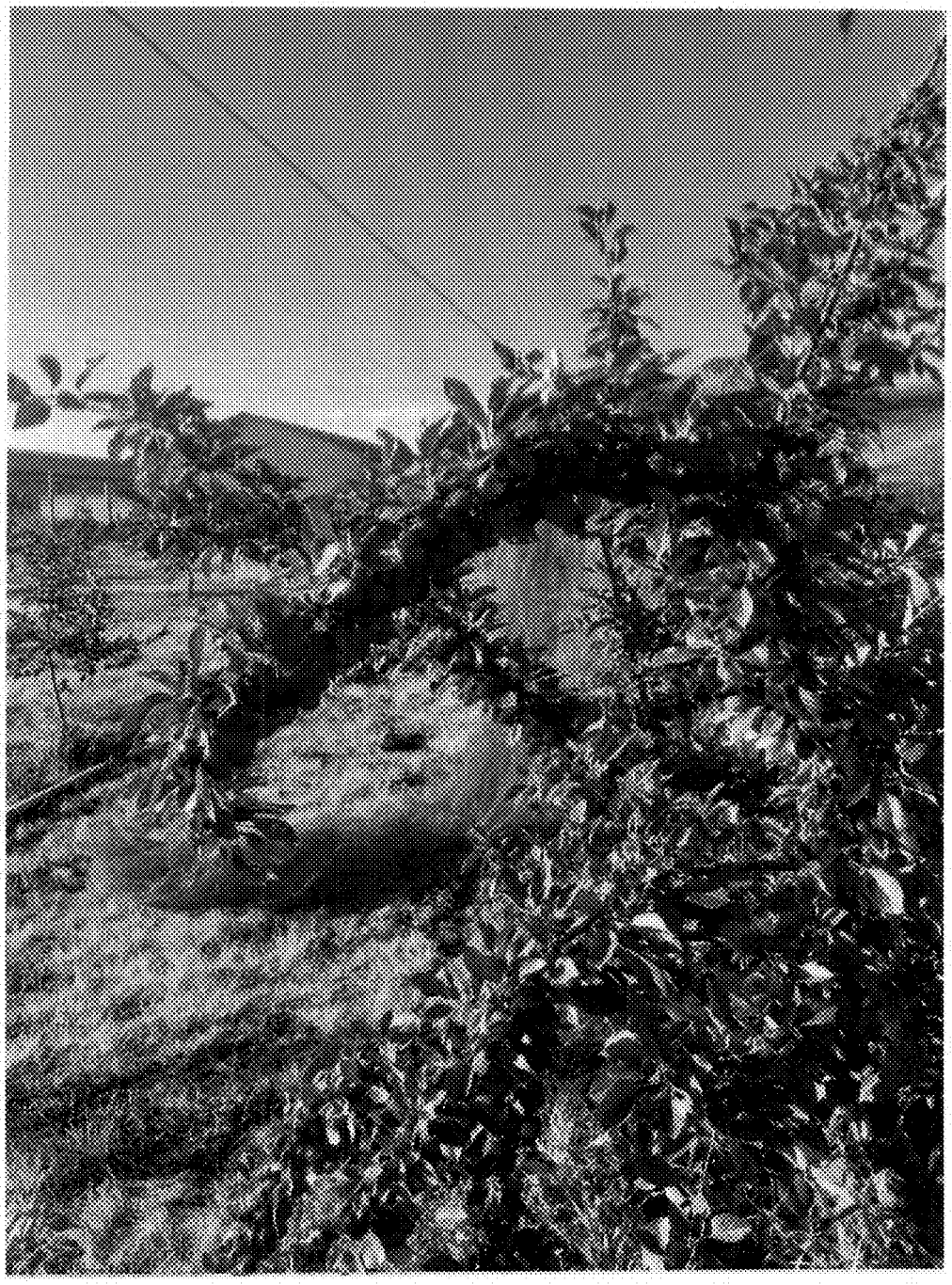
FIG. 8. A photographic illustration showing the tart cherry tree 'FE' with ripe cherries on Aug. 20, 2022.
Figure 9:
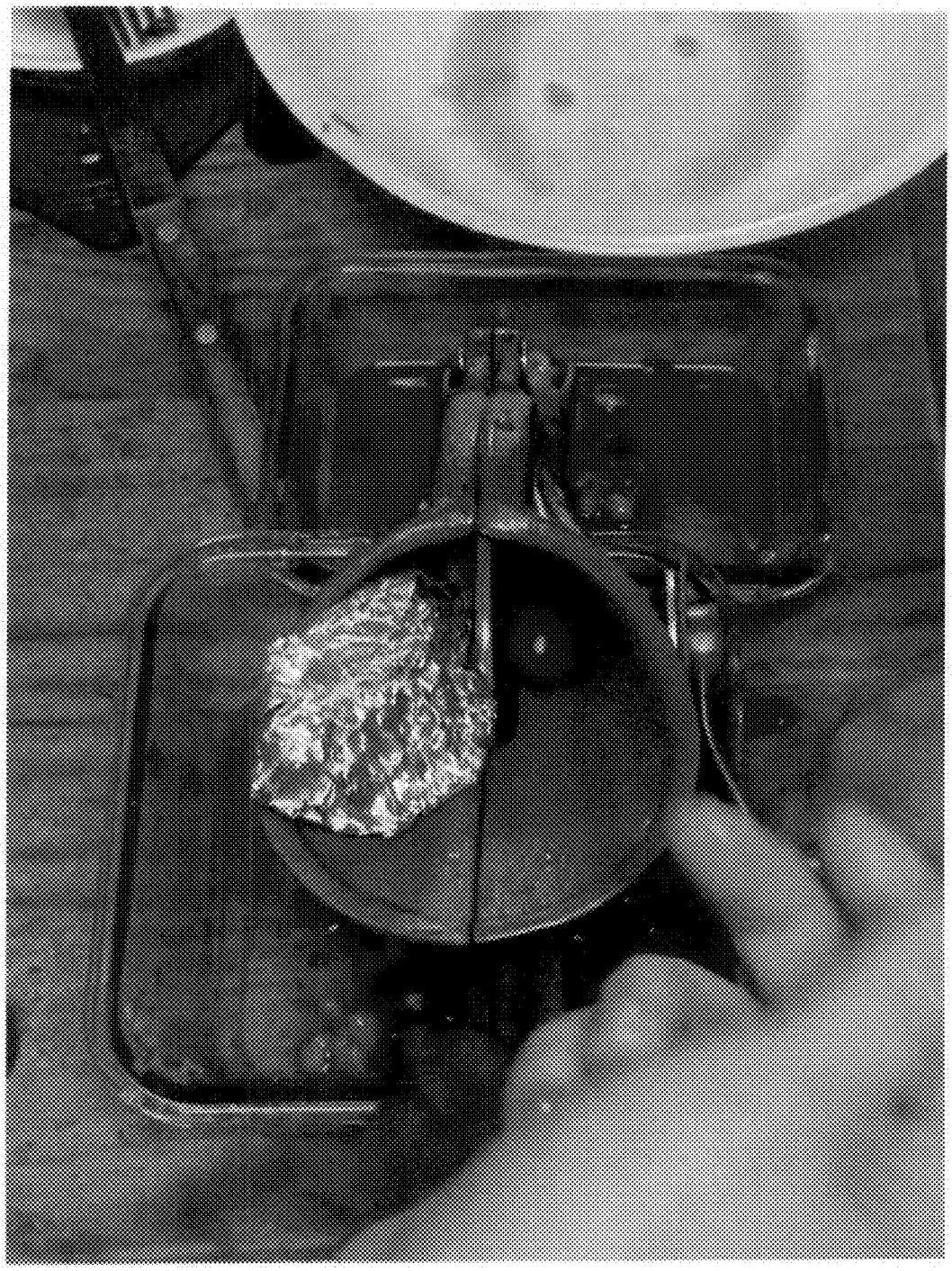
FIG. 9. A photographic illustration of the cherries of tart cherry tree 'FE' being destoned and showing that the juice is red and that the flesh of the cherry is yellow.
Figure 10:
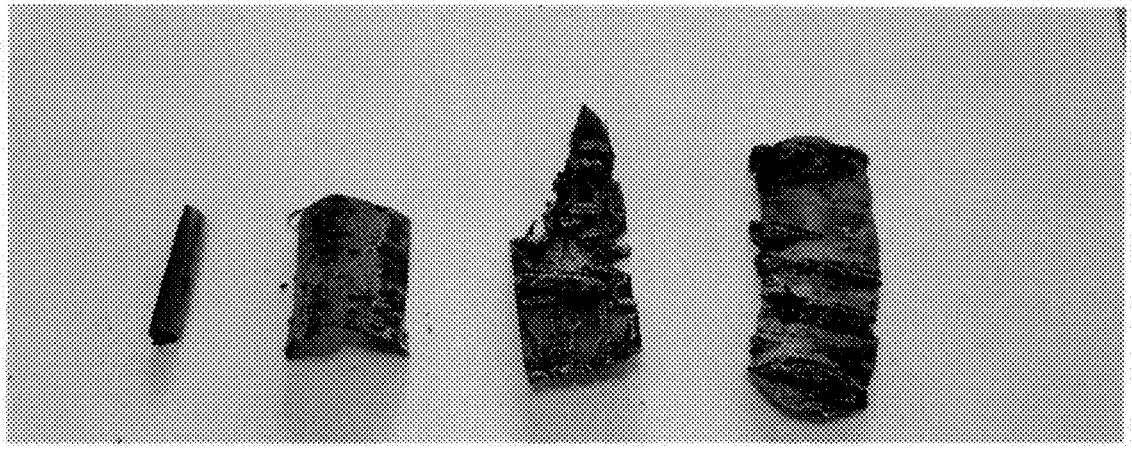
FIG. 10. A photographic illustration showing tree bark of tart cherry tree 'FE' over time.

Figure 7, continued.
(B)
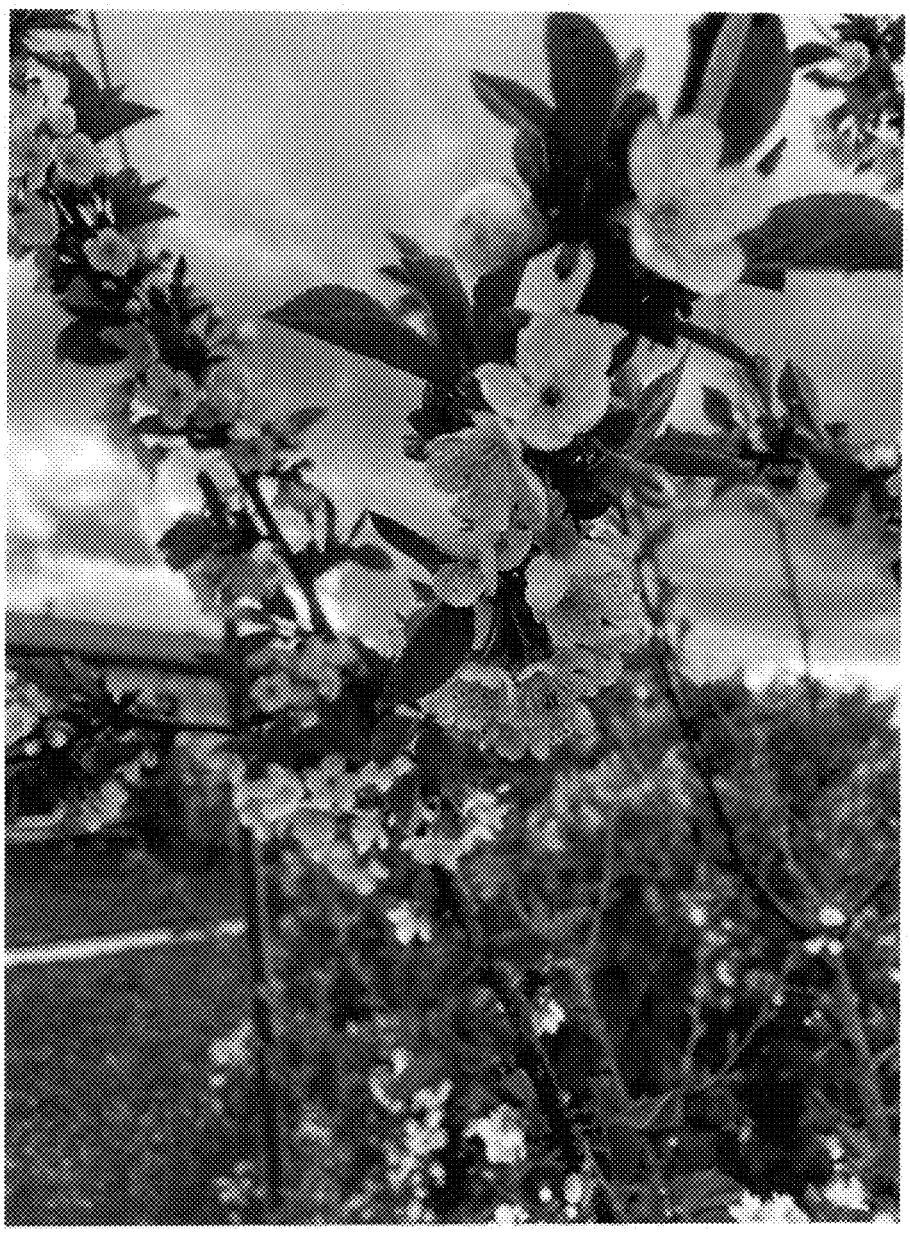

1 Year 2-3 Years 3-6 Years 10 Years Plus